(12) United States Patent
Sordo et al.

(10) Patent No.: US 11,534,521 B2
(45) Date of Patent: Dec. 27, 2022

(54) VOLATILE SUBSTANCE DISPENSING DEVICE AND FABRICATION METHOD THEREOF

(71) Applicant: Zobele Holding S.P.A., Trento (IT)

(72) Inventors: Livio Sordo, Trento (IT); Cedric Morhain, Cerdanyola de Valles/Barcelona (ES); Stefano Deflorian, Trento (IT)

(73) Assignee: ZOBELE HOLDING S.P.A, Trento (IT)

( * ) Notice: Subject to any disclaimer, the term of this patent is extended or adjusted under 35 U.S.C. 154(b) by 0 days.

(21) Appl. No.: 16/334,842

(22) PCT Filed: Sep. 21, 2016

(86) PCT No.: PCT/EP2016/072423
§ 371 (c)(1),
(2) Date: Mar. 20, 2019

(87) PCT Pub. No.: WO2018/054458
PCT Pub. Date: Mar. 29, 2018

(65) Prior Publication Data
US 2020/0023093 A1  Jan. 23, 2020

(51) Int. Cl.
*A61L 9/12* (2006.01)

(52) U.S. Cl.
CPC .......... *A61L 9/12* (2013.01); *A61L 2209/131* (2013.01); *A61L 2209/133* (2013.01)

(58) Field of Classification Search
CPC ................ A61L 9/12; A61L 2209/131; A61L 2209/133; A01M 29/12; A01M 1/2044;
(Continued)

(56) References Cited

U.S. PATENT DOCUMENTS

| 4,804,142 | A |   | 2/1989 | Riley |           |
|-----------|---|---|--------|-------|-----------|
| 5,518,790 | A | * | 5/1996 | Huber | B32B 27/36 |
|           |   |   |        |       | 428/35.2  |

(Continued)

FOREIGN PATENT DOCUMENTS

| DE | 602004002539 | 8/2007 |
|----|--------------|--------|
| EP | 0093262      | 7/1979 |

(Continued)

OTHER PUBLICATIONS

International Search Report dated Apr. 18, 2017 in co-pending PCT/EP2016/072423.

(Continued)

*Primary Examiner* — Tuongminh N Pham
(74) *Attorney, Agent, or Firm* — Sandberg Phoenix & von Gontard PC (57) ABSTRACT

A volatile substance dispensing device (101) and method of fabrication thereof based on a container (201) sealed by a membrane layer (220) with at least one perimetral channel (103) which prevents lateral diffusion of the volatile substance during storage. The at least one perimetral channel (103) is at least partially filled with blocking means such as glue (303) or a protrusion (302) of a separation layer (230) produced by applying heat welding during fixation to the container (201). The dispensing device (101) further comprises a removable barrier layer (240) on top of the separation layer (230).

20 Claims, 5 Drawing Sheets

(58) Field of Classification Search
CPC .............. B65D 75/32; B65D 75/326; B65D 2575/3245; B65D 75/30–34; B65D 75/20; B65D 45/30; B65D 43/14; B65D 43/06; B65D 43/065; B65D 25/008; B65D 77/2004; B65D 77/2008; B65D 77/2016; B65D 77/202; B65D 77/2024; B65D 77/2012; B65D 2543/00435; B32B 3/20; B32B 27/08; B65B 31/028
See application file for complete search history.

(56) References Cited

U.S. PATENT DOCUMENTS 6,460,720 B1 * 10/2002 Massey .................. B29C 65/18
                                                             220/359.1
7,267,243 B2 * 9/2007 Steg .................. B65D 43/0214
                                                             220/359.4
2003/0168521 A1 * 9/2003 Skalitzky .................. A61L 9/03
                                                             239/57
2006/0000923 A1 1/2006 Martens et al.
2006/0016718 A1 * 1/2006 Buss .................. B65D 83/0463
                                                             206/531

FOREIGN PATENT DOCUMENTS

| EP | WO03101500 | 12/2003 |
| EP | WO2013/014078 | 1/2013 |
| EP | 2687237 | 1/2014 |
| JP | 3030711 | 2/2000 |

OTHER PUBLICATIONS

International Search Report dated Oct. 31, 2013 from EP2687237.
International Search Report dated Dec. 4, 2012 from WO2013014078.
International Search Report dated Nov. 26, 2002 from WO2003101500.
International Search Report dated Jul. 26, 1983 from EP00093262.

* cited by examiner

VOLATILE SUBSTANCE DISPENSING DEVICE AND FABRICATION METHOD THEREOF

CROSS REFERENCE TO RELATED APPLICATION

This is a U.S. national stage of International Patent Application Serial No. PCT/EP2016/072423 filed Sep. 21, 2016, which application is entirely incorporated herein by reference.

FIELD OF THE INVENTION

The present invention generally relates to volatile material dispensers, and more specifically, to a dispenser utilizing a membrane for progressive diffusion of the volatile material.

BACKGROUND OF THE INVENTION—RELATED ART

Membrane-based air fresheners have become an increasingly popular alternative for providing controlled dispensing of volatile substances into the ambient air. Among many other examples, U.S. Pat. No. 7,213,770 B2 discloses a dispensing system based on permeable membranes which is attachable to a frame and comprises a plurality of protrusions that prevent excessive gas concentration in delicate surface. U.S. Pat. No. 7,530,503 B2 presents a foldable laminar element with a dispensing membrane and a hook that enables various configurations for the installation of the device. Finally, US 2005/0127538 A1 discloses a device which relies on an external air current, such as a car ventilation outlet to enhance evaporation and diffusion of the volatile substance through the membrane.

Most common systems are based on a polyolefin monolithic membrane, that is, a non-microporous membrane, which is provided in a multi-layer structure together with a barrier material. The multilayer is sealed on the container containing the fragrance in a single step, and the barrier is removed by peeling by the user. This approach is easy to fabricate, but presents limited efficiency and is only compatible with certain kinds of perfumes. Nevertheless, the low permeability of the fragrance through the membrane advantageously enables the perfume to pass through the thin membrane wall but not through the sealing flange (typical thickness around 2 to 5 mm). This prevents evaporation during the storage of the product.

Membranes with higher transportation rates have also been proposed. However this also implies a higher transportation rate through the sealing flanges. Therefore, during storage, slight evaporation may occur through the perimeter of the membrane. This is the case of recently-developed microporous systems, working by capillarity. The perimetral flange is able to transport the volatile substance without any limitations along distances of several millimetres, the perimetral flange hence becoming a quite open system which cannot guarantee refill stability (i.e, absence of weight loss) during storage.

Therefore, there is still the need of membrane-based volatile substance dispersers and refills, which can provide high transportation rates while preventing perimetral leakage of the produce.

SUMMARY OF THE INVENTION

The current invention solves the aforementioned problems by disclosing a membrane-based volatile substance dispenser, such as an air-freshener refill, with perimetral channels for preventing evaporation of the produce through the laterals of the device.

In a first aspect of the invention, a volatile substance dispensing device is disclosed comprising a container of the volatile substance, preferably thermoformed, sealed by a multilayer structure comprising the following:

A membrane layer which, when the device is open, progressively diffuses the volatile substance into ambient air. In a first preferred option, the membrane comprises a microporous film. In a second preferred option, the membrane layer comprises a monolithic permeable polymer, more preferably also comprising a mechanical reinforcement substrate under the membrane layer.

A removable barrier layer which, prior to removal, prevents diffusion of the volatile substance. During first use, the user removes the barrier layer by peeling it. The barrier layer separates from the membrane thanks to a separation layer. The barrier layer preferably comprises an aluminium layer and a plastic layer.

The separation layer, located between the membrane layer and the barrier layer, which facilitates the removal of said barrier layer. Preferably, the separation layer has low internal cohesive mechanical resistance and separates along its thickness, remaining part on the membrane layer and part on the barrier layer.

The membrane layer further comprises at least one perimetral channel at least partially filled by blocking means, preferably implemented with a polymeric material, preventing the lateral diffusion of the volatile substance. In a preferred option, the membrane layer may comprise a plurality of concentric perimetral channels. The perimetral channel or channels are preferably located on top of a perimetral welding flange, and preferably have a width between 0.15 mm and 3 mm.

Two preferred options for the blocking means are disclosed:

A protrusion of the separation layer into the channel of the membrane layer, for example produced by heat welding.

An impermeable polymeric resin typically applied into the channel before joining the container and the multilayer structure. In a preferred option, the polymeric resin comprises a transversal cut that defines the outer edge of the device.

In a second aspect of the present invention, a fabrication method of a volatile substance dispenser is disclosed, comprising the following steps:

Welding a membrane layer, a separation layer and a removable layer to a container of the volatile substance. The membrane layer, separation layer and removable layer are provided in a way that results in the characteristics disclosed for said layers in the first aspect of the present invention. The welding is preferably performed by heat welding.

Cutting one or more perimetral channels in the membrane layer. The cutting step is preferably performed by laser cutting.

Filling at least partially the one or more perimetral channels with blocking means that prevent lateral diffusion of the volatile substance. In a first preferred option, the filling step preferably comprises applying polymeric resin to the channel, and more preferably, curing the resin with ultraviolet exposure.

More preferably, a transversal cut may be performed through the polymeric resin, said cut defining the edge of the dispenser. Also preferably, a plurality of dispensers may be positioned adjacently during fabrication, sharing the same material layers, and being later separated by the transversal cut performed through the polymeric resin. In a second preferred option, the filling step comprises melting the separation layer by applying heat and pressure during welding, until said separation layer partially or fully fills the channel.

Notice that any preferred option or particular embodiment of the device of the invention may be applied to the method of the invention and vice versa.

The described device and method of the invention provide membrane-based volatile substance dispensing with high transport rates and safe storage without perimetral evaporation. They also provide easy fabrication and use, as well as a robust structure. These and other advantages will become apparent in the light of the detailed description of the invention.

BRIEF DESCRIPTION OF THE DRAWINGS

For the purpose of aiding the understanding of the characteristics of the invention, according to a preferred practical embodiment thereof and in order to complement this description, the following figures are attached as an integral part thereof, having an illustrative and non-limiting character.

DETAILED DESCRIPTION OF THE INVENTION

The matters defined in this detailed description are provided to assist in a comprehensive understanding of the invention. Accordingly, those of ordinary skill in the art will recognize that variation changes and modifications of the embodiments described herein can be made without departing from the scope and spirit of the invention. Also, description of well-known functions and elements are omitted for clarity and conciseness.

Note that in this text, the term "comprises" and its derivations (such as "comprising", etc.) should not be understood in an excluding sense, that is, these terms should not be interpreted as excluding the possibility that what is described and defined may include further elements, steps, etc.

Figure 1:
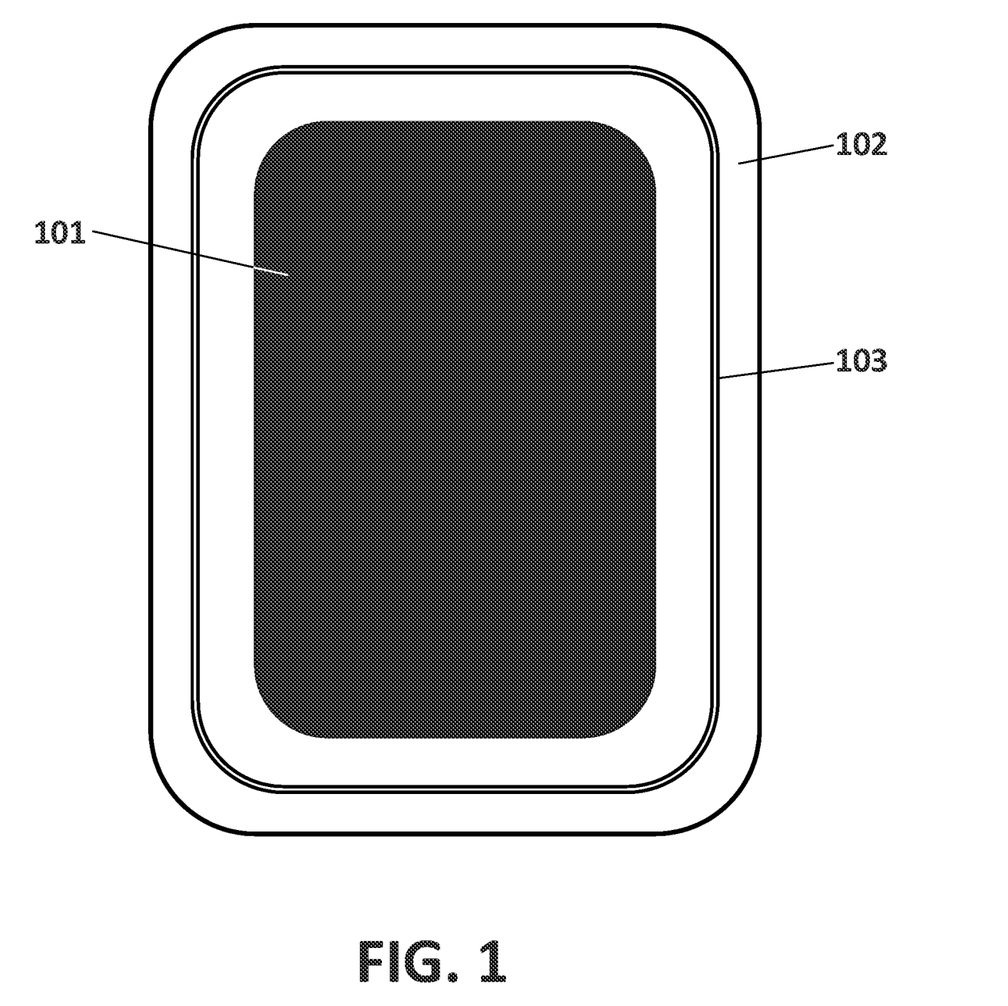
FIG. 1 shows a schematic depiction of a dispenser with a single perimetral channel, according to a particular embodiment of the invention.
Figure 2:
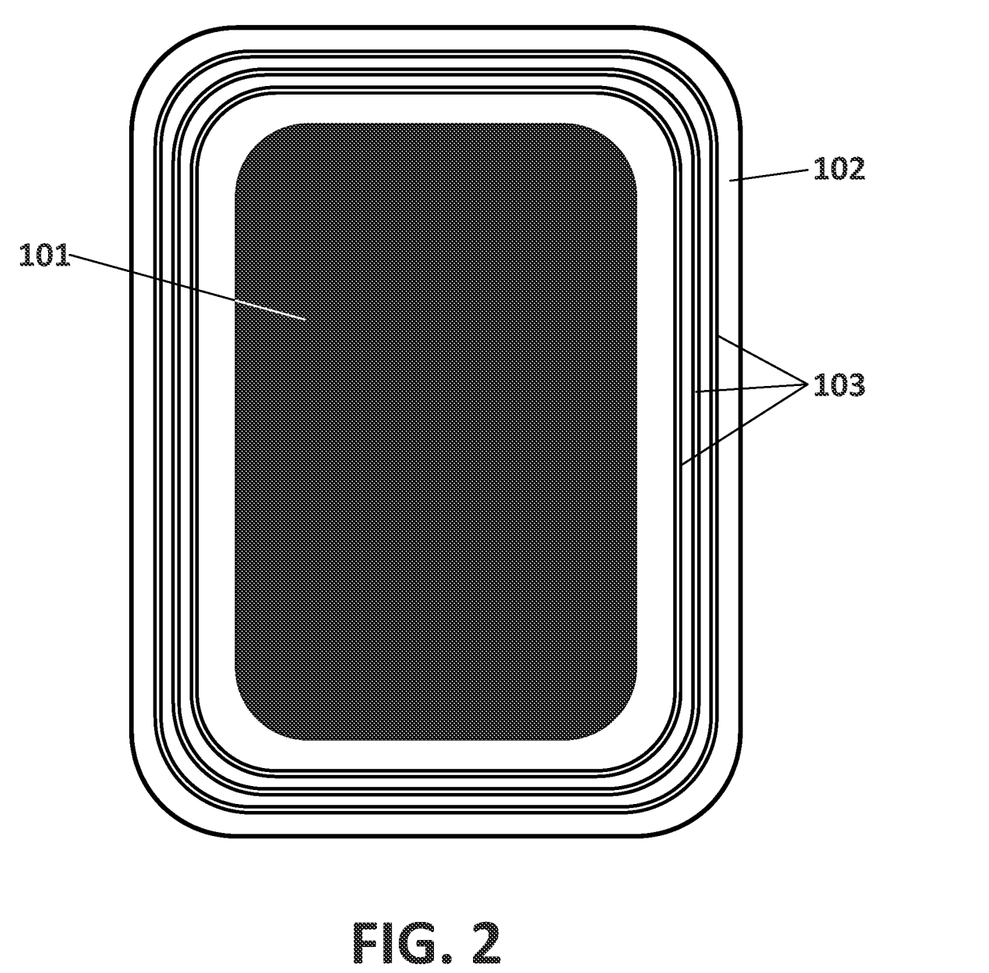
FIG. 2 presents a schematic depiction of a dispenser with three concentric perimetral channels, according to a particular embodiment of the invention.

FIG. 1 shows a frontal view a preferred embodiment of the volatile substance dispensing device 101 of the invention comprising a single perimetral channel 103, located on top of the perimetral welding flange 102 of the thermoformed device. The channel 103 follows a closed continuous line in the external region of the device 101, close to the border of said device 101 but maintaining at least some margin from said border. That is, the membrane layer is present on both sides of the channel 103. Notice that the particular geometry of the channel 103 may vary depending on the particular shape of the device and particular design choices. The channel 103 preferably occupies the full thickness of the membrane layer, although particular embodiments with a channel 103 only partially cutting the membrane thickness may be implemented. Furthermore, several concentric channels may be included in a single device, as exemplified by FIG. 2, hence further reducing liquid transport along the welding flange during storage and consequent weight loss.

Figure 3:
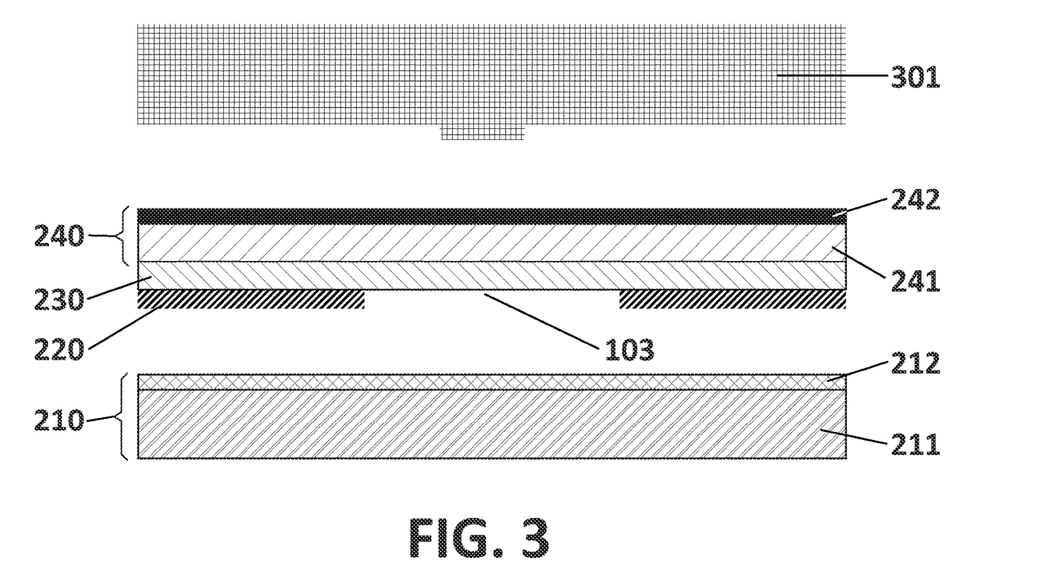
FIG. 3 illustrates a first fabrication process by heat welding of a particular embodiment of the dispenser of the invention.

FIG. 3 presents a lateral view of the dispensing device 101 during fabrication by heat welding. Two separate parts are provided, namely a thermoformed container 210 and a multilayer element comprising a membrane layer 220, a separation layer 230 and a removable barrier layer 240. A welding tool 301 for fixing both parts together is also represented.

The thermoformed container 210 may be implemented by combining a PET (Polyethylene terephthalate) layer 211 and a PE (Polyethylene) layer 212. The container 210 stores the volatile substance in liquid form for its progressive dispensing through the membrane layer 220, preventing its diffusion through any other surface of the device 101.

The membrane layer 220 may be implemented with different alternative technologies:

A microporous film, such as polyethylene, polypropylene, ultra high molecular weight polyethylene, polytetrafluoroethylene, or any other microporous material known in the state of the art.

A monolithic layer of a polymer with high permeability to the volatile substance to be used, such as ethylene-vinyl acetate copolymers, ionomers, polyurethane, or a wide range of thermoplastic elastomers. Additionally, this monolithic film can be mechanically reinforced by a fibrous substrate placed on the other side of the membrane layer 220 opposite to the separation layer 230.

The channel 103 is preferably performed by laser cutting, although other cutting techniques known in the state of the art may be used. The channel preferably has a width between 0.15 to 3 mm. The channel 103 is later filled with a polymeric material having low transport capacity of the volatile substance.

In this case, the separation layer 230 is made from a thermoplastic material having a reduced adhesion to the membrane layer 220, which melts when heat is applied. The thickness of the separation layer 230 is at least equal to the thickness of the membrane layer 220 and is preferably higher than said thickness of the membrane layer 220. Notice that the term "reduced" in this context should be understood as that the strength of adhesion between separation layer 230 and the membrane layer 220 is high enough to stay in place during storage and before first use, but low enough to allow separation when a user manually pulls from the barrier layer 240. The mechanical resistance of the adhesion between membrane layer 220 and separation layer 230 shall be lower than the mechanical resistance of the membrane layer 220 and barrier layer 240, and shall be low enough to circumvent the need of any external tool to separate the layers.

The barrier layer 240 preferable comprises a material having high barrier properties to the volatile substance, such as an aluminium layer 241, and a plastic layer 242 for mechanical reinforcement, such as PET.

The welding tool 301 is adapted to heat and melt the separation layer 230 during the welding process. In this molten state, the material of the separation layer 230 can flow and substantially fill the gap of the membrane layer 220. Furthermore, the welding tool 301 presents a protrusion with a higher depth in an area substantially corresponding to the channel 103 in order to force the material in that area to flow better and fill better the gap in the membrane layer 220. By "substantially", it should be understood that the extra depth in the welding tool 301 falls inside the gap in the membrane during the welding process. So for example, for a gap of 3 mm, with a machine that has a positioning precision of 1 mm, the maximum extra depth in the welding tool shall be 1 mm in order to always fall inside the gap. Although the cutting of the membrane and the filling of the resulting gap can be done in an offline process, it may be advantageously done during a Form Fill Seal process.

Figure 4:
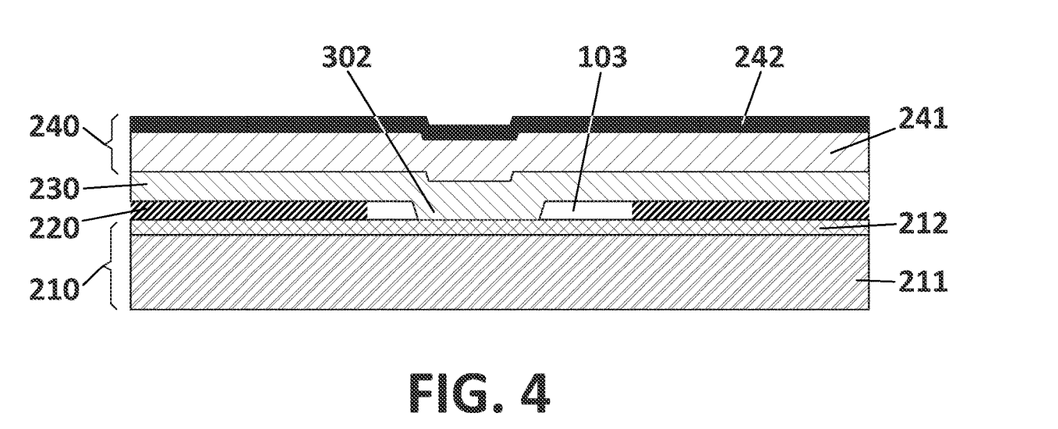
FIG. 4 depicts the dispenser resulting from the fabrication method of FIG. 3.

FIG. 4 presents the device 101 resulting from the fabrication process presented in FIG. 3, according to particular embodiments of the device and method of the invention. After heat welding and melting of the separation layer 230, the protrusion 302 of said separation layer 230 now fills the channel 103, preventing lateral diffusion of the volatile substance. A welding flange 102, for example of 5 mm, is finally performed on the refill.

As a non-limiting example, some particular materials and dimensions for this options are hereby provided. Thermoformed container 210 is based on PET/EVOH/PE with a thickness of 500 μm (EVOH: Ethylene vinyl alcohol). Membrane layer 220 is a Polyethylene microporous of 50 μm thickness. Separation layer 230 is a 100-μm-thick PP layer. Barrier layer 240 comprises a 20-μm-thick Aluminium layer and a 20-μm-thick PET layer. PE membrane is cut by a laser to a width of 3 mm. Laser is set to cut precisely the depth of the PE membrane.

Figure 5:
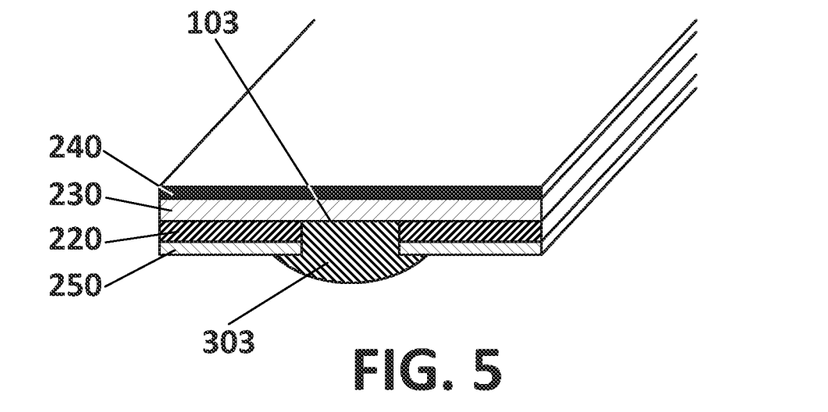
FIG. 5 presents a second fabrication process with impermeable polymeric resin of a particular embodiment of the dispenser of the invention.

FIG. 5 exemplifies an alternative fabrication method in which the plastic material that fills the channel 103 is a polymeric resin 303. In this case, the separation layer 230 is preferably implemented with a paper layer. A ribbon of resin 303 is applied in the channel 103 created by the cut. Polymeric resin application may be carried out, for example, by a motorised three-axis nozzle. The width of the ribbon is preferably slightly wider that the channel 103 cut in the membrane (for example a 1.5 mm ribbon for a 1 mm cut). The polymeric resin 303 is preferably of the kind of epoxy or acrylic glue, UV curable. A UV light is applied to the glue between application of the glue and welding of the multilayer structure on the thermoformed container 210. Optionally, a second dose of UV can be applied after the welding to complete glue curing.

Figure 6:
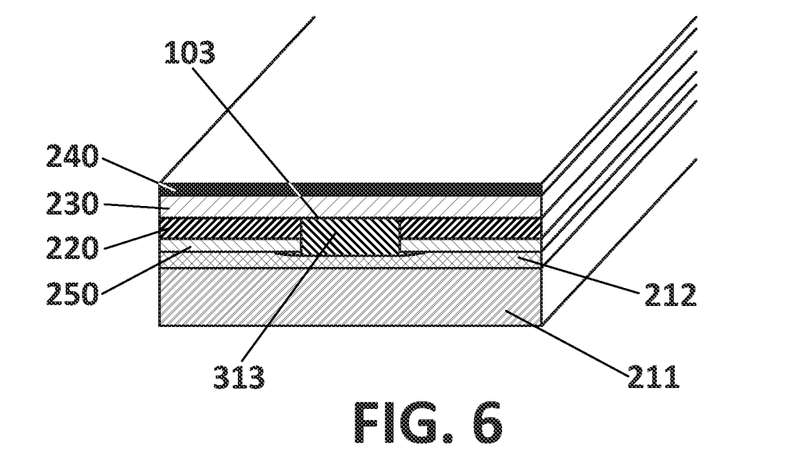
FIG. 6 shows the dispenser resulting from the fabrication method of FIG. 5.

FIG. 6 shows the resulting device of FIG. 5 after joining the multilayer structure to the container 210. As a non-limiting example, some particular materials and dimensions for this options are hereby provided. Membrane layer 220 is a microporous UHMWPE (Ultra-high-molecular-weight polyethylene) with a thickness of 200 μm. Said membrane layer 220 is laminated or glued to a paper layer of 40 gsm (Grams per Square Meter), which is also glued on the other side to a 20 μm Aluminium/20 μm PET layer. The glue used is a polyurethane reactive hot melt with a dosage of 15 gsm. Microporous UHMWPE is cut in a continuous line of 1 mm width by a laser. The laser cut goes through the whole membrane thickness and also through the paper layer.

Figure 7:
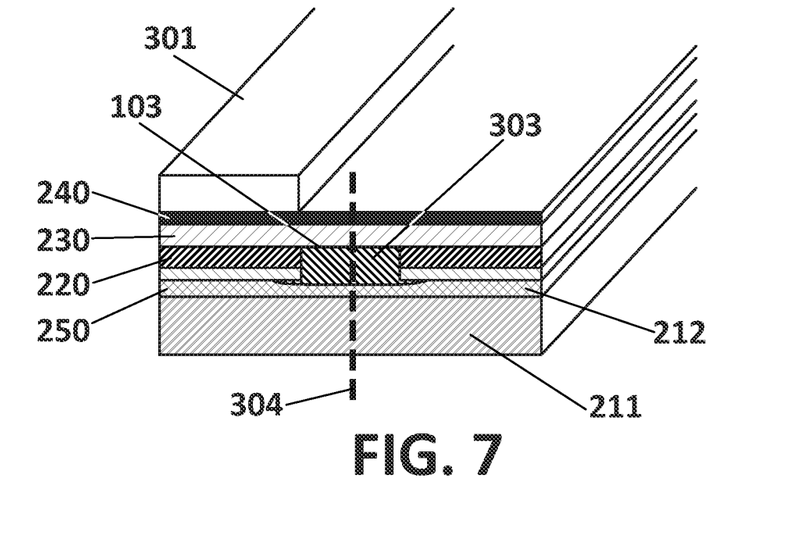
FIG. 7 depicts a third fabrication process with a transversal cut through the impermeable polymeric resin of a particular embodiment of the dispenser of the invention.
Figure 8:
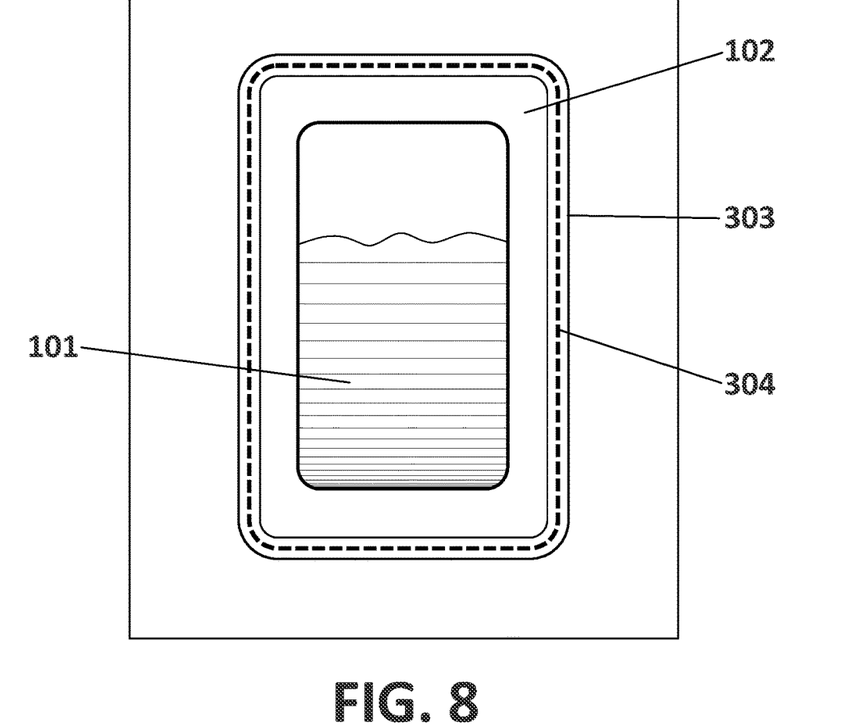
FIG. 8 further illustrates said third fabrication process with a frontal view of the dispenser.

FIG. 7 presents an alternative embodiment of the fabrication method of the invention, resulting in a subsequent alternative embodiment of the device of the invention. In this case, after filling the channel 103 with the polymeric resin 303 (and curing if necessary), a transversal cut 304 is performed through the whole thickness of the device 101 at the position of said polymeric resin 303. Therefore, the transversal cut 304 determines the edge of the device 101, and reduces the size of the device 101 by removing all layers outside the channel 103. In case of multiple channels 103, the transversal cut 304 is performed across the outermost channel 103. This process is also illustrated in FIG. 8, where the remaining materials of the device 101 outside the dashed line of the transversal cut 304 are discarded.

Figure 9:
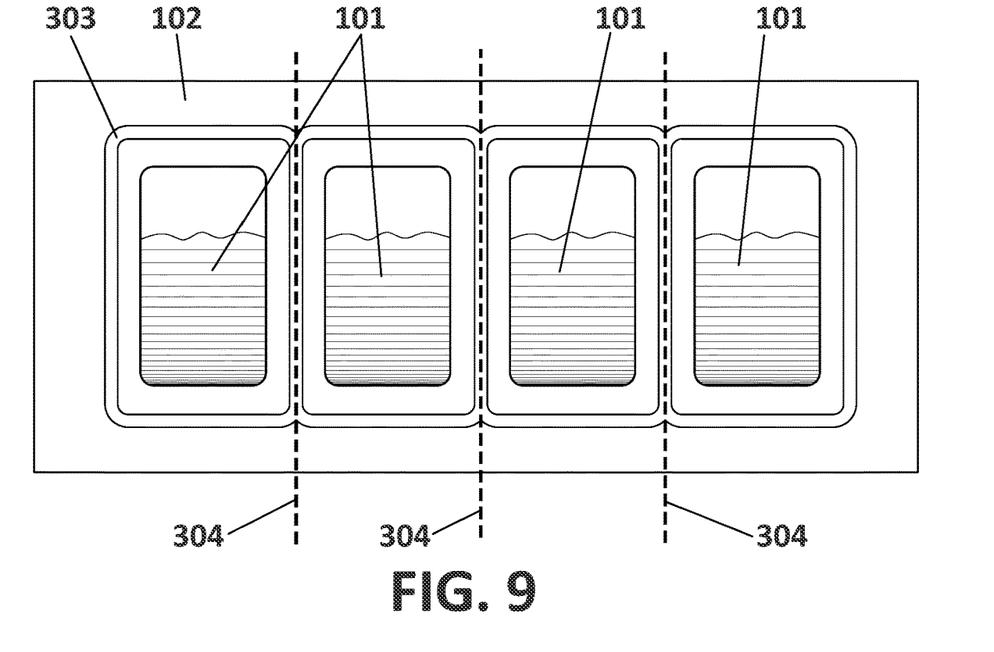
FIG. 9 presents a fourth fabrication process in which the transversal cut separates adjacent dispensers according to a particular embodiment of the invention.

FIG. 9 illustrates yet another embodiment of the fabrication method of the invention, resulting in a subsequent embodiment of the device of the invention, also based on performing a transversal cut 304 through the whole thickness of the device 101 at the position of the polymeric resin 303 filling the channel 103. In this case, however, two or more devices 101 are fabricated simultaneously and adjacently by sharing either all or some of the material layers (container 210, material layer 220, separation layer 230 and barrier layer 240). Each two adjacent devices 101 share a channel 103 filled with the polymeric resin 303. Therefore, when the transversal cut 304 is performed through said shared channel 103, the two adjacent devices 101 are separated. This fabrication method further optimizes the amount of discarded material outside the transversal cut 304.

What is claimed is:

1. A volatile substance dispensing device (101) comprising:
   a container (210), the container containing a volatile substance;
   a membrane layer (220) sealing the container (201), the membrane layer (220) being adapted to progressively diffuse the volatile substance through the membrane layer and into ambient atmosphere of the container;
   a removable barrier layer (240) preventing the diffusion of the volatile substance through the membrane layer; and
   a separation layer (230) between the membrane layer (220) and the barrier layer (240), the membrane layer (220) comprising at least one perimetral channel (103) extending through a full thickness of the membrane layer (220), the perimetral channel (103) is at least partially filled with plastic blocking means preventing the diffusion of the volatile substance through the membrane layer and across the perimetral channel.

2. The device (101) according to claim 1 wherein the blocking means comprises a protrusion (302) of the separation layer (230).

3. The device (101) according to claim 1 wherein the container (210) is a thermoformed container with a perimetral welding flange (102) and in that the at least one perimetral channel (103) is located on top of the welding flange (102).

4. The device (101) according to claim 1 wherein the membrane layer (220) comprises a microporous film.

5. The device (101) according to claim 1 wherein the membrane layer (220) comprises a monolithic permeable polymer.

6. The device (101) according to claim 2 wherein the protrusion (302) extends from the separation layer (230) and fills the at least one perimetral channel (103), preventing lateral diffusion of the volatile substance through the membrane layer (220).

7. The device (101) according to claim 3 wherein the protrusion (302) extends from the separation layer (230) to the welding flange (102) and fills the at least one perimetral channel (103), preventing lateral diffusion of the volatile substance through the membrane layer (220).

8. A volatile substance dispensing device (101) comprising:
a container (210), the container being configured for containing a volatile substance;
a membrane layer (220) on the container (210), the membrane layer (220) being able to diffuse a volatile substance contained in the container (210) through the membrane layer (220) and into an ambient environment of the container (210);
a barrier layer (240) on the membrane layer (220), the barrier layer (240) being removable from the membrane layer (220);
a separation layer (230) between the membrane layer (220) and the barrier layer (240), the separation layer (230) enabling the barrier layer (240) to be manually pulled and peeled away from the membrane layer (220); and
the membrane layer (220) having at least one perimetral channel (103) in the membrane layer (220), the at least one perimetral channel (103) being filled with a blocking means that prevents diffusion of the volatile substance contained in the container (210) through the membrane layer (220) and into an ambient environment of the container (210).

9. The device (101) of claim 8, further comprising:
the blocking means comprises a protrusion (302) from the separation layer (230) that extends into the perimetral channel (103) in the membrane layer (220) and blocks diffusion of the volatile substance contained in the container (210) through the membrane layer (220).

10. The device (101) according to claim 9, further comprising:
the protrusion (302) extends from the separation layer (230) and fills the at least one perimetral channel (103), preventing lateral diffusion of the volatile substance through the membrane layer (220).

11. The device (101) according to claim 8 further comprising:
the container (210) is a thermoformed container with a perimetral welding flange (102); and
the at least one perimetral channel (103) is on the perimetral welding flange (102).

12. The device (101) according to claim 11, further comprising:
the protrusion (302) extends from the separation layer (230) to the welding flange (102) and fills the at least one perimetral channel (103), preventing lateral diffusion of the volatile substance through the membrane layer (220).

13. The device (101) of claim 8, further comprising:
the at least one perimetral channel (103) is one of a plurality of concentric perimetral channels (103) in the membrane layer (220).

14. The device (101) of claim 8, further comprising:
the membrane layer (220) is comprised of a microporous film.

15. The device (101) of claim 8, further comprising:
the membrane layer (220) comprises a monolithic permeable polymer.

16. A volatile substance dispensing device (101) comprising:
a container (210), the container (210) being configured for containing a volatile substance, the container (210) having a top flange (102);
a multi layer structure on the top flange (102), the multi layer structure sealing the container (210), the multi layer structure comprising a membrane layer (220), a separation layer (230) and a barrier layer (240);
the membrane layer (220) being on the top flange (102) of the container (210), the membrane layer (220) being able to diffuse a volatile substance through the membrane layer (220), the membrane layer (220) having a channel (103) in a full thickness of the membrane layer (220), the channel (103) being a perimetral channel in the membrane layer (220) on the top flange (102) of the container (210), the perimetral channel (103) forming a gap in the membrane layer (220) with the membrane layer being present on both sides of the gap;
the separation layer (230) being on the membrane layer (220);
the barrier layer (240) being on the separation layer (230), the barrier layer (240) preventing diffusion of the volatile substance through the membrane layer (220), the barrier layer (240) being removable from the separation layer (230) and the membrane layer (220) by manually pulling and peeling the barrier layer (240) from the separation layer (230) and the membrane layer (220); and
blocking means (302) in the gap in the membrane layer (220), the blocking means (302) preventing lateral diffusion of a volatile substance from the container (210), through the membrane layer (220) and across the top flange (102) of the container (210).

17. The device (101) of claim 16, further comprising:
the blocking means (302) is a protrusion (302) of the separation layer (230) extending into the gap in the membrane layer (220).

18. The device (101) of claim 16, further comprising:
the separation layer (230) being separable along a thickness of the separation layer (230) with a part of the separation layer (230) remaining on the membrane layer (220) and a part of the separation layer (230) remaining on the barrier layer (240) when the barrier layer (240) is removed from the separation layer (230) and the membrane layer (220).

19. The device (101) of claimed 16, further comprising:
the membrane layer (220) comprises a microporous film.

20. The device (101) of claim 16, further comprising: the membrane layer (220) comprises a monolithic permeable polymer.

* * * * *